United States Patent
Franklin et al.

(10) Patent No.: US 6,974,804 B2
(45) Date of Patent: Dec. 13, 2005

(54) ESTERS

(75) Inventors: Kevin Ronald Franklin, Wirral (GB); Andrew Hopkinson, Wirral (GB); Nicholas Webb, Wirral (GB); Michael Stephen White, Wirral (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 62 days.

(21) Appl. No.: 09/982,077

(22) Filed: Oct. 17, 2001

(65) Prior Publication Data
US 2002/0072506 A1 Jun. 13, 2002

(30) Foreign Application Priority Data
Oct. 17, 2000 (GB) .............................. 0025437

(51) Int. Cl.$^7$ .................. A61K 31/715; A61K 7/32; A61K 7/38; C07H 13/04; C07H 13/06
(52) U.S. Cl. .................. 514/53; 514/54; 536/115; 536/119; 536/124; 424/65; 424/66; 424/68; 424/400
(58) Field of Search .................. 536/115, 119, 536/124; 424/65, 66, 68, 400; 514/53, 54

(56) References Cited

U.S. PATENT DOCUMENTS

| | | | |
|---|---|---|---|
| 3,969,087 A | 7/1976 | Saito et al. ................ | 44/7 |
| 4,673,570 A | 6/1987 | Soldati ..................... | 424/66 |
| 4,725,430 A | 2/1988 | Schamper et al. .......... | 424/66 |
| 4,725,432 A | 2/1988 | May ........................ | 424/66 |
| 4,822,602 A | 4/1989 | Sabatelli .................. | 424/65 |
| 4,948,578 A | 8/1990 | Burger et al. ............. | 424/68 |
| 4,954,333 A | 9/1990 | Ward ....................... | 424/66 |
| 5,169,626 A | 12/1992 | Tanner et al. ............. | 424/66 |
| 5,429,816 A | 7/1995 | Hofrichter et al. ........ | 424/66 |
| 5,486,566 A | 1/1996 | Katsoulis ................. | 524/773 |
| 5,587,153 A | 12/1996 | Angelone, Jr. et al. ..... | 424/66 |
| 5,744,130 A | 4/1998 | Guskey et al. ............ | 424/66 |
| 6,248,312 B1 * | 6/2001 | Franklin et al. .......... | 424/400 |
| 6,458,344 B2 * | 10/2002 | Franklin et al. .......... | 424/65 |

FOREIGN PATENT DOCUMENTS

| | | |
|---|---|---|
| EP | 512 770 | 10/1996 |
| WO | 92/19222 | 11/1992 |
| WO | 93/23008 | 11/1993 |
| WO | 97/11678 | 4/1997 |
| WO | WO-99/33853 A2 * | 7/1999 |
| WO | 00/61079 | 10/2000 |
| WO | 00/61082 | 10/2000 |

OTHER PUBLICATIONS

Cosmetics and Toiletries, *Deodorant/Antiperspirant–Sticks*, 1990, vol. 105, p. 75–78.
GB Search Report in a GB Application, GB 0025437.5.
Bull. Chem. Soc. Japan (1995), 68(12), 3423–8.
Chem. Pharm. Bull. (1981), 29(2), 505–13. Abstract.
Co–pending U.S. Appl. No. 09/982,150, filed Oct. 17, 2001, Franklin et al.
Co–pending U.S. Appl. No. 09/978,954, filed Oct. 17, 2001, Grainger et al.
European Search Report in an EP application 01 30 7826.
Takada et al., "Discotic Columnar Liquid Crystals In Oligosaccharide Derivatives III. Anomeric Effects On The Thermo–Mesomorphic Properties Of Cellobiose Octa–Alkanoates" Liquid Crystals, vol. 19, No. 4, pp. 441–448.

* cited by examiner

Primary Examiner—James O. Wilson
Assistant Examiner—Everett White
(74) Attorney, Agent, or Firm—Karen E. Klumas

(57) ABSTRACT

Acylated cellobiose compounds (CHME) which satisfy the formula;

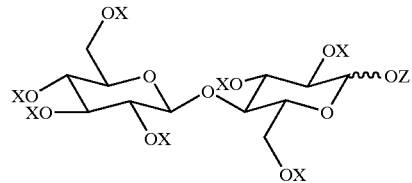

wherein
X represents an acyl group (R—CO—) or H, Z represents an acyl group (R'—CO—) or H and not more than a minority of X+Z residues represent H,
R represents a saturated or unsaturated, linear or branched chain hydrocarbon residue of 5 to 31 carbon atoms and
R' represents a residue, different from R, which is:
(i) a saturated or unsaturated, linear or branched chain hydrocarbon residue of 1 to 31 carbon atoms, or (ii) an aromatic hydrocarbon residue, or (iii) a cycloaliphatic hydrocarbon, each optionally substituted.
CHME esters are particularly suited to thickening or structuring a water-immiscible liquid, for example, a phase in a cosmetic formulation, such as antiperspirant or deodorant formulations, eg water in oil emulsions and especially translucent ones.

51 Claims, No Drawings

ESTERS

The present invention relates to esters and in particular to esters of cellobiose, compositions containing them, and their use as structurants.

BACKGROUND

Many compositions intended for topical application to skin, including a number for various parts of the body, such as face, gums, hands, limbs, feet, torso, underarm, breasts, genitalia, hair and other parts of the body, comprise one or more active agents are distributed within or otherwise supported by a carrier fluid. Although it is possible, in many instances, that such compositions are in the form of lotions, it is often desirable that the active ingredient in such compositions, be it for medical or for cosmetic purposes, remains substantially localised in the region of the body to which it has been topically applied. In order to assist this to happen and also to enable alternative dispensers for the composition to be employed, the carrier fluid can be thickened or structured, for example by introducing one or more materials for that purpose. Thickened or structured compositions commonly adopt the form of firm sticks, or soft solids and creams. In such circumstances, the materials are often referred to as structurants or gelants and may sometimes alternatively be called thickeners, depending on the final form of the composition. The carrier fluid may comprise water and/or a water-miscible organic liquid and alternatively or additionally a water-immiscible liquid.

In general, the choice of structurants or thickeners tends to vary in accordance with the physical nature of the carrier fluid and in particular on whether it is water-miscible or immiscible. The present invention is directed more particularly towards materials which are capable of structuring a water-immiscible liquid, which may act by itself as carrier for an active ingredient or comprise a water-immiscible phase in an emulsion or micro-emulsion.

Many materials have been proposed for structuring or thickening a water-immiscible liquid-phase of a composition intended for topical application to humans. These have included waxes natural waxes, such as paraffin waxes or those typically extracted from vegetation, such as candelilla wax, or glyceride waxes, or produced by chemical treatment of natural oils, for example hydrogenation of castor oil, or produced by extracted from fauna, such as beeswax or spermaceti wax, or derivatives or synthetic variants of them. Others include fatty alcohols, eg linear C18 or C22 alcohols. Other materials are polymeric, such as polysiloxane waxes, or polysiloxane elastomers, or various polyamide/polysiloxane copolymers.

In the closing years of the 20th century, a number of structurants were identified which the present inventors classify as fibre-forming. These include 12-hydroxy stearic acid, various amino acid amides, including particularly, combinations of sterols and sterol esters, including particularly β-sitosterol and γ-oryzonol, derivatives of threitol, diamide derivatives of cyclohexane, and acylated derivatives of cellobiose. Each of the various structurants has to a greater or lesser extent its particular benefits and its intrinsic disadvantages, either in absolute or relative terms. These properties can include the ability of the material to gel or otherwise structure the carrier liquid, including the resultant hardness and stability, and the sensory properties and appearance of the resultant composition, the latter being of great importance for cosmetic compositions.

One of the most desirable class of structurants comprises acylated cellobiose, as described in pending PCT application No PCT/GB 00/01228, now published as WO 00/61079, particularly for structuring a water-immiscible liquid in a cosmetic compositions, including especially antiperspirant and deodorant compositions. Said PCT application describes various benefits for the acylated cellobiose structurant and exemplifies many compositions demonstrating such benefits. In said PCT application, it has been disclosed that the cellobiose can adopt either an a α or β configuration, preferably the former, and various preferences are given for both the number of acyl substituents of the cellobiose nucleus and the chemical constitution of the substituents. The description of alternatives included the choice of an aliphatic acyl substituent, whether it is linear or branched and its chain length. Acylated cellobiose materials were exemplified in which identical acyl substituents were employed. The most highly preferred acylated cellobiose described therein is cellobiose octanonanoate.

Continuing research into the properties of acylated cellobiose materials and compositions structured using them has shown that variations in the structurants can result in changes to various of the properties of the structured compositions, including amongst other things the thermal stability of the final structured material, the resistance of the structurant to crystallisation in situ, and the clarity and hardness of the composition.

α-cellobiose octanonanoate has been shown to be an extremely good structurant for water-immiscible liquids, including silicone fluids and water-immiscible emollient liquids employed in many cosmetic compositions. However, ongoing research into the acylated cellobiose structurants has indicated that its thermal stability could be improved and that long term storage can lead to a gradual reduction in clarity. This would appear from studies to be associated with crystallisation of the structurant. Either effect conveys self-evident disadvantages. Loss of structural strength with time limits the shelf life of the product and a reduction in clarity can be taken by consumers as a visual cue that efficacy has been impaired. Consumer formulations can take a long time to pass through conventional manufacture and distribution channels and can sometimes also spend a long time on consumers' shelves before or during use, so that it is desirable to find ways of ameliorating or overcoming any negative effects that would otherwise arise during storage. It will, of course, be recognised that any changes made should endeavour not to sacrifice any of the other beneficial properties of the products.

However, many compositions are desirably translucent or transparent and the controlled hardness of the composition remains an important characteristic. Consequently, any change made to the formulation or alternative selection made from the class of acylated cellobiose materials should endeavour to minimise or even overcome and reverse any impairment to the other properties of the structurant which might arise when seeking to improve one of the properties. By way of example, measures to improve stability against in situ crystallisation can reduce hardness. Mixtures of the materials can be contemplated and then some trade-off in the performance of the structurant mixture compared with its constituents has been observed.

It is an object of the present invention to provide an alternative acylated cellobiose which demonstrates an attractive combination of properties, particularly in the context of acting as a structurant for a water-immiscible liquid.

It will be understood, however, that although the material of the instant invention is contemplated especially for use in cosmetic formulations, its potential use is much wider, including the structuring of a water-immiscible liquid to make a cream, soft solid or stick for any other purpose. Such other purposes could include topical medicaments, topically applied veterinary products or animal cosmetics and waxes or polishes.

BRIEF DESCRIPTION OF THE INVENTION

According to a first aspect of the present invention there is provided as a new compound, an acylated cellobiose satisfying the general formula:

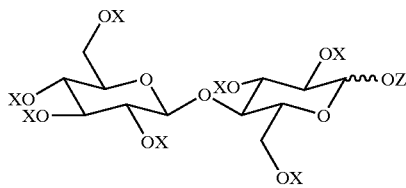

in which X represents an acyl group (R—CO—) or H, Z represents an acyl group (R'—CO—) or H and not more than a minority of X+Z residues represent H, R represents a saturated or unsaturated, linear or branched chain hydrocarbon residue containing from 5 to 31 carbon atoms and R' represents a residue which is different from R and which is:

(i) a saturated or unsaturated, linear or branched chain hydrocarbon residue containing from 1 to 31 carbon atoms, optionally substituted or;

(ii) an aromatic hydrocarbon residue, optionally substituted or;

(iii) a cycloaliphatic hydrocarbon, optionally substituted.

The Z substituent is at the anomeric position.

Such an ester herein in which R differs from R' is sometimes referred to as a CHME.

Such materials, ie CHMEs, demonstrate an excellent combination of properties rendering those materials particularly suitable for structuring or thickening water-immiscible liquids, enabling them to be employed in the manufacture of base gels for cosmetic or medical actives and particularly for translucent base gels. The benefits accrue by selecting substitution R' at the anomeric carbon which is different from that of the other alkyl groups R.

For example, by comparison with the employment of various cellobiose octaesters, advantageously, improvements in one or more of the following properties can be seen, namely clarity, thermal stability and resistance against in situ crystallisation, whilst not sacrificing hardness.

According to a second aspect of the present invention there is provided a method for the preparation of an acylated cellobiose as described in the first aspect hereinabove comprising the step of reacting an acylated cellobiose having general formula 2

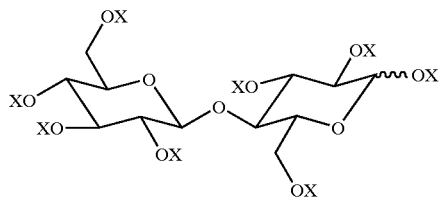

in which X represents an acyl group (R—CO—) or H, H being not more than a minority of X residues and R represents a saturated or unsaturated, linear or branched chain hydrocarbon residue containing from 5 to 31 carbon atoms with an acylating agent containing a residue R' as described hereinabove preferentially at the anomeric carbon of the cellobiose.

In this aspect, either the hydroxyl group at the anomeric carbon atom is acylated, or the acyl group R—CO— at the anomeric carbon atom is transesterified.

In a third aspect of the present invention there is provided the use of an acylated cellobiose as described in the first aspect hereinabove for thickening or structuring a water-immiscible liquid, thereby forming a cream, soft solid or solid.

In a fourth aspect of the present invention, there is provided a base composition in the form of a cream, soft solid or solid containing a structurant or thickener an acylated cellobiose as described hereinabove in the first aspect.

In a related fifth aspect of the present invention, the base composition of the fourth aspect additionally contains an active cosmetic, medical, or veterinary agent.

DETAILED DESCRIPTION OF THE INVENTION AND PREFERRED EMBODIMENTS

Herein the acylated cellobiose compounds satisfy the formula shown below:

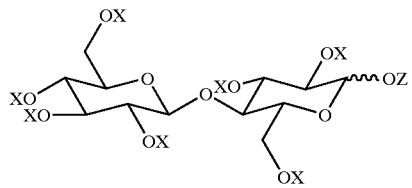

When X and Z represent respectively —COR and —COR' in this formula, R represents a saturated or unsaturated, linear or branched chain hydrocarbon residue which contains from 5 to 31 carbon atoms, often up to 18 carbon atoms, preferably from 7 and 12 carbon atoms and especially 8 or 9 carbon atoms. Preferably R residues are saturated and desirably are linear. Most desirably, all R groups are the same. It will be recognised that in practice the alkyl substituent of a specified chain length in an acylating agent can contain impurity levels of isomers or close homologues. For example, when R is nominally octyl, the substituent can comprise as impurities a low proportion, typically not more than 5% of iso octyl and n-heptyl/n-nonyl groups.

In this formula, R' represents an aliphatic, aromatic or cycloaliphatic residue. R' can be alkyl, alkaryl, aryl, or aralkyl, optionally substituted. In many desirable embodiments, R' is non-aliphatic when R is aliphatic.

The residue R' when aliphatic can comprise a saturated or unsaturated, linear or branched chain hydrocarbon residue containing from 1 to 31 carbon atoms, more desirably linear, and preferably from 2 to 22 carbon atoms. The R and R' residues are different from each other, so that R'0 is often selected from residues having a maximum chain length in the ranges of up to R–2 carbons or from R+2 carbons, and conveniently in the ranges of from 1 to 6 and 13 to 22 carbon atoms. Particularly desirable short chain alkyl R' residues include methyl, ethyl, and propyl. The alkyl groups within R' can optionally be fluorinated or substituted by an aryl group such as those described hereinafter or by a cycloaliphatic group such as those described hereinafter or by an amine or amide group. The substituted aliphatic residue R' desirably contains not more than 31 and particularly not more than 22 carbon atoms.

When R' represents or contains an aromatic hydrocarbon residue, particularly an aryl residue, suitable examples comprise phenyl, naphthyl and biphenyl residues. The aryl group can comprise 1 or a plurality of nuclei, which may be fused or not fused. The aryl nucleus or nuclei therein can be substituted, for example by an alkyl or alkoxy group containing up to 20 carbon atoms or a halo group such as fluoro or a nitro group or an alkyl ester, alkylamine or alkylamido group. The substituted aromatic residue R' desirably contains not more than 26 carbon atoms.

When R' represents a cycloaliphatic hydrocarbon residue, suitable examples include cyclohexane and cyclooctane. The cycloaliphatic nuclei can be substituted for example by an alkyl or alkoxy group containing up to 20 carbon atoms or by an aryl group such as described above.

R' can comprise an alkyl, aryl, cycloalkyl, alkaryl, aralkyl or cycloalkylaryl residue.

The acylated cellobiose materials according to the present invention can adopt either of the α or β anomeric forms or mixtures thereof. In a number of highly desirable embodiments, for example those in which R' constitutes a saturated hydrocarbon residue, such as cyclohexyl, or linear C4 to C10 alkyl which differs from the R residue, the CHME comprises at least 60 molar % in the β anomeric form, particularly at least 80 molar %, and some especially preferred CHMEs are at lest 90 molar % in the β anomeric form. In other desirable embodiments, for example those in which R' constitutes an unsaturated hydrocarbon residue, such as benzoyl or 4-Biphenoyl, the CHME preferably is at least 90 molar % in the β anomeric form.

Preferably, the acylated cellobiose is acylated by a total of greater than six and in many instances greater than seven acyl substituents, R—CO—+R'—CO—, on average, and especially by at least 95 molar % of total acylation. In practice, we have found that acylation often occurs preferentially at cellobiose carbons other than at its anomeric carbon atom, so that the former carbons tend towards being fully acylated, commonly at least six of the seven X locations representing R—CO—, and in many instances all or substantially all seven locations representing R—CO—, whilst anomeric carbon may be, and commonly is, acylated to a lesser proportion.

It is desirable that the anomeric carbon is acylated to at least 50%, preferably at least 60% and more preferably is at least 75% acylated, and most desirably in conjunction with X representing at or substantially 100% R—CO— (normally at least 6 out of seven locations, and preferably greater than 97%). It is particularly desirable to employ CHMEs in which there is not only a high extent of acylation at the anomeric carbon, but also simultaneously a high molar proportion of the ester is in the β anomeric form, each of which feature has been described more precisely hereinbefore.

An especially suitable sub-set of CHMEs comprises esters in which i) each R substituent represents a linear octyl residue, ii) the anomeric position is acylated to a high proportion and preferably at least 75 molar %, and iii) a high proportion of and preferably at least 80 molar % of the CHME is in the β anomeric form.

When contemplating the use of the cellobiose esters in general and the invention esters in particular for preparing translucent gels of water-immiscible fluids, such as silicone fluids or other water-immiscible fluids mentioned herein, it is desirable to select those materials which have a relatively high fibre dissolution temperature (FDT). Advantageously, many of the invention esters herein exhibit an FDT of at least 48° C. and especially advantageous invention esters are those having an FDT of at least 51° C., because they tend to produce gels having greater storage stability.

The acylated cellobiose materials of the present invention may be used as a sole or primary structurants or may be used as minor or supplementary structurant in conjunction with one or more of the classes of structurants that are mentioned hereinafter. By way of example, the invention structurants can be used together with an acylated cellobiose described in PCT/GB 00/01228, in which the anomeric acyl group is the same as at least some of the other acyl groups, ie R=R', such as cellobiose octanonanoateor, especially, cellobiose octadecanoate.

It is especially desirable to employ acylated cellobiose materials identified herein (CHMEs) in which all the R substituents are identical and are n-nonyl or particularly n-octyl and at least 75% of substituents at the anomeric carbon are R' (ie at least 75 molar % acylation at the anomeric position) and =cyclohexyl, phenyl, naphthyl or methyl and particularly cyclohexyl. Such especially desirable CHMEs preferably are at least 80 molar % in the β anomeric form.

Material Preparation

One convenient and general method for making the acylated cellobiose compounds of the present invention comprises the step of transesterifying a corresponding acylated cellobiose in which the acyl substituents —COR and —COR' are identical. Such a process in practice can be two step, the first step of which comprises preparing an octaesterified cellobiose, for example by a process as described hereinbelow. The second step of such a process comprises reacting the octaester with an acylating agent containing a —COR' residue, capable of displacing the residue —COR, if needed in the presence of a strong acylating catalyst. The resultant product often comprises a proportion of residual R—CO— residues at the anomeric carbon atom.

A related method comprises acylating the corresponding partially acylated cellobiose with an acylating agent containing a —COR' residue, where needed in the presence of an acylating catalyst, the anomeric carbon being partly or preferably wholly or substantially wholly substituted by an hydroxyl group. Such a substrate can be obtained, for example, by deacylating wholly or partly a cellobiose octester. Consequently, the invention mixed ester cellobiose compounds can be made in a three step process comprising the steps of first making an octaester in which the acyl substituent —COR' at the anomeric carbon is the same as at the other cellobiose carbons, R—CO—, secondly removing the anomeric acyl substituent, and then re-acylating at the anomeric position with a different acyl substituent.

In one way of carrying out the first step, be it for either the two or three step processes indicated above, cellobiose (commonly D-(+)-cellobiose) is reacted with a molar excess of an acylating agent, often a substantial excess, such as an acid chloride, RCOCl, carboxylic acid $RCO_2H$ or acid anhydride $(RCO)_2O$ and, where necessary, an acylation catalyst. The R groups are as hereinbefore described. For example, when using an acid as acylating agent, the catalyst can desirably be derivable from an acid having a low $pK_a$ such as an anhydride $(R"OCO)_2O$, often in a significant molar excess. The R" group is desirably a polychlorinated or preferably polyfluorinated alkyl, such as trifluoromethyl. The acylating agent, eg carboxylic acid, is preferably employed at a mole ratio to the cellobiose in the range of at least 50:1 and especially from 60:1 to 100:1. The catalyst is preferably employed with the acid at a mole ratio to the cellobiose of at least 20:1 and particularly from 22:1 to 50:1. The acylation is desirably conducted at an elevated temperature such as above 70° C. and especially approximately 100° C. for a period of at least 2 hours and especially from 3 to 10 hours. The resultant product is substantially or completely acylated, that is to say that at least 90% of the acylatable hydroxyl groups on the cellobiose have been acylated and often at least 95% acylated.

In a variant of the first step, the cellobiose (commonly D-(+)-cellobiose) is reacted with a molar excess of an acylating agent, often a significant excess, such as an acid chloride, RCOCl, in solution in a volatile chlorohydrocarbon such as chloroform, the presence of an excess of a strong base catalyst, such as pyridine, and most preferably in a dry, inert atmosphere. Preferably, the acylating agent is employed in a mole ratio to the cellobiose in the range of from 12:1 to 24:1, from 1.5 to 3 times a stoichiometric amount for octa-acylation. The base catalyst is commonly employed in a mole ratio to the cellobiose of from 6:1 to 12:1. The acylation step is desirably carried out at a mildly elevated temperature, such as from 40 to 75° C., and often at from 45 to 60° C. The reaction is advantageously monitored via HPLC and/or proton NMR and allowed to continue until hepta-acylated cellobiose is no longer detectable. Such reaction period is often in the range of from 10 to 30 hours. The acylation product can be recovered by cooling to ambient and precipitation in methanol. This method is particular applicable for the preparation of esters predominantly in the β anomeric form.

In the second step in the above-mentioned three step process, the acylated cellobiose produced in the first step or the variant, i.e. in predominantly α or β anomeric form or a mixture thereof, is partially de-acylated preferentially at the anomeric carbon. One method comprises reacting the fully acylated cellobiose with a mixture of a low molecular weight aliphatic acid, (C1–C4) and especially acetic acid with an alkylene diamine such as in particular ethylene diamine, at a low concentration in THF (tetrahydrofuran), such as from 4 to 15% by weight acylated cellobiose. The acid employed in the second step has a higher $pK_a$ than the catalyst in the first step. The reaction preferably employs an approximately equimolar ratio of acid to acylated cellobiose, such as in the range of 0.9 to 1.2:1 and a small molar excess of diamine to acylated cellobiose, such as from 1.6 to 2.5:1. The reaction can conveniently be carried out in at or about ambient temperature, e.g. 20 to 30° C. for a long reaction time, often of at least 12 hours and particularly from 24 to 60 hours, or at a mildly elevated temperature such as up to 45° C. for a commensurately shorter period such as selected in the range of from 5 to 10 hours. The resultant partially deacylated material can be recovered by extraction into a haloalkane solvent such as dichloromethane and acid washed. After drying, it is recrystallisable from a THF/methanol mixture.

In the third step, the partially de-acylated cellobiose is re-acylated. The re-acylation can employ a carboxylic acid, an acid chloride, or an anhydride.

In the first variant of this third step, the cellobiose is reacted with an at least equimolar amount of an acid chloride of formula R'COCl, preferably a small molar excess of from 1.1 to 1.5:1, in the presence of at least an equimolar amount of triethylamine and preferably a small molar excess of from 1.1 to 1.5:1. The reaction is desirably conducted at or within 10° C. of reflux temperature, suitably for at least 1 hour and preferably from 2 to 4 hours. Desirably, the reaction is permitted to continue until at least a predetermined extent of acylation at the anomeric carbon, such as at least 80% and often at least 90% has occurred. In this first variant, the resultant CHME is predominantly in the β anomeric form, the exact proportions of the α and β forms depending on the acyl substituent and process conditions adopted.

In the second variant of this third step, the partially deacylated cellobiose is reacted with an substantial excess of a carboxylic acid of formula $R'CO_2H$, such as a mole ratio of at least 50:1 and particularly from 60 to 100:1 in the presence of a significant molar excess of a strong acid catalyst such as that employed in the first step and preferably in a mole ratio to the cellobiose of at least 20:1 and especially from 22:1 to 50:1. The reaction is preferably carried out at elevated temperature, such as especially above 90° C. and particularly at about 100° C. The reaction period is desirably at least 4 hours and is especially from 5 to 10 hours. Desirably, the reaction is permitted to continue until at least a predetermined extent of acylation at the anomeric carbon, such as at least 80% and often at least 90% has occurred. In this second variant, the resultant CHME is predominantly in the α anomeric form, the exact proportions of the α and β forms depending on the acyl substituent and process conditions adopted.

In the third variant for carrying out the third step, the partially-deacylated cellobiose is reacted with an anhydride of formula $(R'CO)_2O$. The reaction is conveniently carried out in a hydrocarbon solvent having a boiling point of at least 80° C., such as toluene. The reaction preferably employs an excess anhydride, especially in a mole ratio to the cellobiose of at least 2:1, and often from 2.5 to 10:1.

Water-immiscible liquid

The water-immiscible liquid, which in many embodiments acts as a carrier for a disperse solid or liquid phase, normally comprises one or a mixture of materials which are relatively hydrophobic so as to be immiscible in water. Some hydrophilic liquid may be included in the water-immiscible liquid, to the extent that it is soluble or miscible with the water-immiscible liquid and provided the overall carrier liquid mixture is still. immiscible with water. It will generally be desired that this carrier is liquid (in the absence of structurant) at temperatures of 15° C. and above. It may have some volatility but its vapour pressure will generally be less than 4kPa (30 mm Hg) at 25° C. so that the material can be referred to as an oil or mixture of oils. More specifically, it is desirable in some embodiments, that at least 80% by weight of the hydrophobic carrier liquid should consist of materials with a vapour pressure not over this value of 4kPa at 25° C.

It is preferred, e.g. for use in cosmetic formulations that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ $m^2$/sec (10 centistokes), and particularly above $10^{-7}$ $m^2$/sec (0.1 centistokes), the linear siloxanes normally exhibiting a viscosity of below $5 \times 10^{-6}$ $m^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic water-immiscible liquid carrier employed in many compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Selected polyalkylaryl siloxanes include short chain polysiloxanes, e.g. tri or tetrasiloxanes containing on average at least one phenyl group per siloxane unit, for example tetraphenyltrisiloxanes. Commercially available non-volatile silicone oils include Dow Corning 556, Dow Corning 200 series and DC704.

The water-immiscible liquid carrier may contain from 0 to 100% by weight of one or more liquid silicones. Some embodiments contain liquid silicones in at least 10%, better at least 15%, by weight of the whole composition. If, silicone oil is used, in some embodiments, volatile silicone preferably constitutes from 10 to 100% of the weight of the carrier liquid. In many instances, when a non-volatile silicone oil is present, its weight ratio to volatile silicone oil is chosen in the range of less than 3:1 such as from 1:3 to 1:40, whereas in certain other embodiments, the proportion of volatile silicone oils is from 0 to less than 10%, so that the weight ratio of non-volatile to volatile silicone oils is greater than 10:1, such as from 15:1 to ∞:1. In other embodiments, liquid silicones are absent, or present in only a small proportion of the water-immiscible phase, such as up to 7 or 8% by weight. Accordingly, a range of mixtures of silicone oils and non-silicone oils can be employed as liquid carrier for structuring by the CHME invention esters. Many of such mixture employ a weight ratio of the silicone to non-silicone oils of from 4:1 to 1:4. The selection of carrier fluids is often made taking into account the refractive index of the components of the carrier fluid mixture, and the refractive index of a particulate active constituent such as an antiperspirant or of a water-miscible phase.

Silicon-free hydrophobic liquids can be used instead of, or in some embodiments in addition to liquid silicones. Silicon-free hydrophobic organic liquids which can be incorporated include volatile or non-volatile liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters, but for some uses, for example antiperspirant formulations, these should be used as only part of the liquid carrier, desirably not above 20%, and possibly less than 10% by weight of the water-immiscible liquid carrier.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols, eg C2–C4 alkyl PPG ethers such as commercial products having CFTA nominally labelled PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid carrier. It is preferred that silicone oil and/or a hydrocarbon oil is present and that the total amount of other liquid carriers, preferably, constitutes up to 50 or 60% for example from 0 to 10% OR 10 to 20% by weight of the water-immiscible carrier liquid.

An especially desired combination of water immiscible carrier liquids comprises a mixture of a silicone liquid such as a cyclomethicone and a hydrocarbon liquid, such as in a weight ratio of the former to the latter of from 3:2 to 1:10, optionally in the presence of an emollient water-immiscible liquid.

Emulsion

Many formulations according to the present invention also contain a more polar disperse phase. In such compositions, the invention acylated cellobiose acts as a structurant in the continuous water-immiscible phase. The disperse phase may be a polar liquid alone or conveniently comprise a solution of an active ingredient, such as an antiperspirant salt.

The hydrophilic disperse phase in an emulsion normally comprises water as solvent and can comprise one or more water-soluble or water-miscible liquids in addition to or as a replacement for water. The proportion of hydrophilic carrier fluid, e.g. water, in the disperse phase, in an emulsion according to the present invention is often selected in the range of up to 60%, and particularly from 10% up to 40% or 50% of the whole formulation.

One class of water-soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxyl group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion, the disperse phase is likely to constitute from 5 to 80 or 85% of the weight of the composition preferably from 5 to 50 or 65%, more preferably from 25 or 35% up to 50 or 65%, while the continuous phase with the structurant therein provides the balance from 15 or 35% up to 95% of the weight of the composition. Advantages can accrue when the internal phase volume constitutes a minor proportion of emulsion, such as from about 30 to 45% by weight. Yet other advantages arise at 45 to 65% internal phase volume. Compositions with high proportion of disperse phase, i.e. from 65 to 85% disperse phase, may also be advantageous. They can give good hardness even though the concentration of esterified saccharide structurant may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 2 or 3% by weight, such as 0.3%, 0.4% or 0.5% by weight, or an amount in between. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10–25, steareth-10–25 (i.e. $C_{16}$ to $C_{18}$ alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups. An especially desirable example of this class is available under the trade name ABIL EM90 for use within the aforementioned ranges of proportions.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPR™, Span™, Tween™, SF1228, DC3225C and Q2-5200.

Antiperspirant Actives

If the composition is an antiperspirant, it will contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_3CH(NH_2)CO_2H$.

It is highly desirable to employ complexes of a combination of aluminium halohydrates and zirconium chlorohydrates together with amino acids such as glycine, which are disclosed in US-A-3792068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives that may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 3 μm.

Optional ingredients

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as triclosan eg Igasan DP300™, Tricloban™, and Chlorhexidine warrant specific mention. A yet another class comprises biguanide salts such as those available under the trade mark Cosmosil™.

A yet further class of antimicrobial which can advantageously be employed herein comprises transition metal chelators, such as amino acids or salts thereof, which chelators have affinity for iron (III), and preferably a binding constant for iron (III) of greater than $10^{10}$, or, for optimum performance, greater than $10^{26}$. The 'iron (III) binding constant' referred to above is the absolute stability constant for the chelator-iron (III) complex. One especially preferred chelator is DTPA (diethylene triamine pentaacetic acid) and salts thereof. Such antimicrobials suppress microbial regrowth. A convenient amount is from 0.35 to 2% by weight.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

A further optional constituent of the formulation comprises one or more secondary structurants which can be employed in addition to the esterified saccharide of the present invention. The amount of such secondary structurants in the formulation is often zero, and usually not more than 15% of the formulation. In many embodiments, it is normally not greater than the amount of the primary structurant.

The secondary structurants employable herein can be non-polymeric or polymeric. Solid linear fatty alcohol and/or a wax may be included but are not preferred. Non-polymeric structurants, sometimes referred to as gellants, can be selected from fatty acids or salts thereof, such as stearic acid or sodium stearate or 12-hydroxy stearic acid. Other suitable gellants can comprise dibenzylidene alditols, e.g. dibenzylidene sorbitol. Further suitable gellants can comprise lanosterol, selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

One especially desirable secondary structurant comprises an esterified cellobiose as described in PCT/GB 00/01228, which description is incorporated herein. Such a structurant is sometimes called an ACB structurant herein. Preferably, the ACB structurant can be represented by the formula:

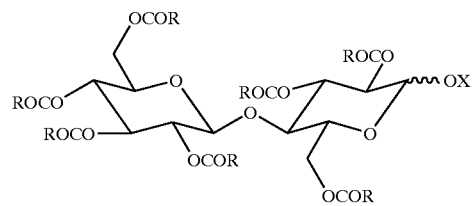

in which R is as defined hereinabove in respect of the invention structurants and X represents either hydroxyl or an acyl group R—CO—. More preferably, the acyl group —COR is at least 50% and especially at least 75% of X. In such ACB structurants, the alkyl group R is preferably octyl or nonyl or preferably may comprise mixtures of R groups having up to 2 fewer or 2 more carbons than an average of 8 to 9 carbons. The substituent —OX is present at the anomeric carbon in the cellobiose. The ACB structurant can be made in either α or β anomers. Highly desirably, the proportion of α anomer in the ACB structurant is greater than 50%, particularly greater than 80% and especially greater than 90%.

Herein, the ACB structurant can be employed advantageously with the primary invention structurant (CHME) in a wide ratio of amounts, such as in a weight ratio thereto of up to 25:1, and in many instances up to 15:1, and in the same or other embodiments in the range of from 1:25, or sometimes from 1:5 or from 1:1. A convenient weight ratio of ACB to CHME is from 5:1 to 12:1. In some particularly desirable formulations, the weight ratio of ACB to CHME is from 65:35 to 85:15.

In a number of very suitable formulations, the ACB is selected from cellobiose octadecanoate esters, especially those of which at least 80 molar %, eg 80 to 95 molar % are the α anomer. In some of such very suitable formulations and in various other suitable formulations, the CHME ester comprises a cellobiose heptanodecanoate monobenzoate ester, and particularly such a CHME which is at least 90 molar % β anomer, such as 93 to 100 molar % β anomer.

Translucent/Transparent Compositions

When a composition of this invention is formulated as an emulsion it is possible to construct the formulation such that the emulsion is translucent or transparent. In order to do this the refractive indices of the water-immiscible continuous phase and the polar or aqueous disperse phase must be matched to each other and the value of refractive index at which they are matched must also approximately match the refractive index of the structurant.

The refractive index of a fibrous network of a structurant can be determined by using that structurant to gel a number of oils or oil mixtures of differing refractive index. The invention acylated cellobiose (CHME) fibrous networks have a refractive index which falls in a range between 1.45 and 1.51 at 22° C.

For the continuous phase, silicon-free water-immiscible liquid oils described hereinbefore generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C. and some non-volatile silicone oils, eg dimethicone oils, similarly have a refractive index of about 1.41 at 22° C., but carrier liquid mixtures with refractive indices in the range from 1.41 to 1.46 can be obtained by mixing volatile or such non-volatile silicone with other oils. Other non-volatile silicone oils containing aryl substitution generally have refractive indices of at least 1.45, for example from 1.45 to 1.48 at 22° C., the oils bearing a high ratio of phenyl substituents to alkyl substituents can enjoy a higher refractive index than 1.48, such as from 1.49 to 1.56. Such other aforementioned non-volatile silicone oils can be included when desired to achieve a carrier liquid mixture having a desired refractive index.

The RI of the structured continuous phase will conveniently be very close to the RI of the carrier liquid (usually a carrier liquid mixture) which is its principal component.

For the disperse phase, a solution of an antiperspirant active salt in water alone will generally display a refractive index below 1.425. The refractive index can be raised by incorporating a diol or polyol into the aqueous solution. It is believed to be beneficial to match the refractive index of a polar disperse phase to that of a structurant network within a continuous phase. Moreover, it can be achieved without using so much diol or polyol as will make the composition excessively sticky.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand- wheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Having described the invention in general terms, specific embodiments thereof will be described more fully by way of example only.

EXAMPLE 1

In this Example, cellobiose heptanonanoate ester compounds according to the present invention and summarised in Table 1 below were made in a three step route, the first two steps of which was common to all variants and the third step of which was carried out by one of three routes. The route is exemplified for cellobiose heptanonanoate esters. Other acylated cellobiose esters were made by substituting the same molar amounts of alternative acylating agents for nonanoic acid.

Step 1. Preparation of cellobiose octanonanoate

Cellobiose was esterified with nonanoic acid to yield the fully esterified product in the form of its α-anomer following a procedure generally as described in Takada et al, Liquid Crystals, Volume 19, No 4, page 441 (1995).

The following materials, obtained from Acros Organics—Fisher Scientific, were used:
D-(+)-cellobiose, 20 grams, 0.058 moles
Nonanoic acid, 591.6 grams, 3.74 moles
Trifluoroacetic anhydride, 297.6 grams, 1.42 moles.

The nonanoic acid was charged into a 2 liter flange pot equipped with an overhead stirrer, water condenser and addition inlet together with the trifluoroacetic anhydride. The resultant clear mixture was stirred up and heated to 100° C. using a silicone oil bath and temperature probe. During heating it was noted that the colour of the reaction mixture darkened and developed a dark brown tinge. After allowing the mixture to stir for one hour at 100° C., the cellobiose was slowly added via a solid powder funnel to the dark activated solution, and a dirty brown suspension was formed which re-dissolved forming a clear black solution within 10–20 minutes.

The reaction flask was then maintained at 100° C. for a total of 6 hours then cooled down to ambient laboratory temperature. Next the contents of the flask were transferred into 2 liters of methanol containing 10% deionised water in an ice-cooled 5 liter beaker. Immediately an off-white solid precipitate came out of solution, this was filtered off and collected. The crude solid was re-crystallised a total of 4 times from a tetrahydrofuran/methanol solution producing a white solid product.

The product was obtained in a quantity of 31.5 g which was a 37% yield. It had a melting point of 110° C.

Step 2. Partial de-acylation

Glacial acetic acid (2.04 g) was added slowly dropwise with stirring into a solution of ethylenediamine (4.09 g) in tetrahydrofuran (THF, 850 cm$^3$). A white precipitate formed which remained during the reaction. α-Cellobiose octanonanoate (50 g) was then added and the whole reaction mixture stirred at room temperature for a total of 48 hours.

At the end of the reaction period, the contents of the flask were transferred to a two liter separating funnel, 350 cm$^3$ of water was added and the mixture extracted with dichloromethane (250 cm$^3$). The organic layer was collected and further washed with successive 350 cm$^3$ portions of (1) dilute HCl (0.1 M), (2) aqueous sodium bicarbonate (1 M) and (3) water.

The resultant organic phase was recovered, dried over anhydrous magnesium sulphate, filtered and the remaining solvent removed by rotary evaporation. A slightly sticky off-white crude solid was obtained. This was then re-crystallised from a mixture of THF/methanol (50:300 cm$^3$). During overnight storage, a white solid precipitated out and was filtered off, dried and collected, yielding 30.5 g of a white free-flowing solid as intermediate product (68% Yield).

Step 3.

3A—Re-acylation with an acyl chloride

This route is exemplified for the benzoate ester, and is useable for all the esters by substituting the other acid chlorides for benzoyl chloride.

A 3 neck 500 cm$^3$ round bottomed flask was charged with cellobiose heptanonanoate (5 g, 3.78×10$^{-3}$ moles) together with 125 cm$^3$ of toluene. The mixture was stirred thoroughly until a clear solution resulted. Next triethylamine (0.479 g, 4.73×10$^3$ moles) was slowly added dropwise to the solution.

Thereafter, Benzoyl Chloride (0.665 g, 4.73×10$^3$ moles) was added slowly and cautiously via a pressure equalising dropping funnel into the reaction mix. When addition of the reagents was complete, the whole reaction solution was heated up to and maintained under reflux conditions for a total of 2–3 hrs. The flask was then removed from the heat and after cooling was filtered to remove the solid triethylamine hydrochloride salt present. A clear straw coloured liquid was obtained. All solvent was then removed by rotary evaporation to give a crude product, a straw coloured gel-like material. The crude product was re-crystallised from THF-MeOH (20 cm$^3$:120 cm$^3$). The resultant product, a white free-flowing solid, was filtered off, collected and dried at 40–45° C. Yield was 3.5 g (65%).

3B—Re-acylation employing an acid/catalyst

This method is exemplified using benzoic acid and can also be used for making the other cellobiose esters by replacing benzoic acid by the appropriate acid.

A 2 neck 250 cm$^3$ round bottomed flask was charged with Benzoic Acid (29.54 g, 0.24 moles) and trifluoroacetic anhydride (19.05 g, 0.091 moles). The mixture was stirred and heated to and maintained at 100° C. for one hour. Cellobiose heptanonanoate (5 g, 3.78×10$^{-3}$ moles) was introduced slowly via a solids addition funnel into the activated solution. After it had added completely, the reaction mixture was maintained at 100° C. stirred for a total of 6 hours. The reaction flask was then cooled down to room temperature. An ice-cooled solution of methanol-water (400 cm$^3$ MeOH:40 cm$^3$ water) was poured into the flask, whereupon a solid precipitate formed immediately, was filtered off and re-crystallised from THF-MeOH (20 cm$^3$:120 cm$^3$). The resultant product was filtered off collected and re-crystallised a second time from THF-MeOH to remove trace acid. The final product, a white solid, was filtered off, collected and dried at 40–45° C. The yield was 3.1 g (58%).

3C—Re-acylation using an anhydride

The method is exemplified using acetic anhydride and the other cellobiose esters can be made by substituting the appropriate anhydride for acetic anhydride.

A 3 neck 500 cm$^3$ round bottomed flask was charged with cellobiose heptanonanoate (5 g, 3.78×10$^3$ moles) and toluene (50 cm$^3$). The mixture was stirred, creating a pale yellow clear solution. Acetic anhydride (1.16 g, 1.13×10$^{-2}$ moles) was added slowly via a pressure equalising dropping funnel. When its addition was complete, the reaction mixture was heated up to 120° C. and refluxed for 6 hrs. The mixture was cooled down to room temperature and all solvent removed by rotary evaporation to yield a crude gel-like solid, which was filtered off and re-crystallised from THF-MeOH (20 cm$^3$:120 cm$^3$), filtered off, and dried at 40–45° C. Yield: 4.4 g (85%).

In Table 1, the substituent listed is at the anomeric carbon, and the % Y listed is the proportion of the anomeric OH which has been converted to the specified acyl group.

The % A (α anomer) and % Y (extent of acylation at the anomeric carbon) can be determined by proton NMR spectroscopy, using a Bruker DRX 500 MHz NMR Spectrometer. The samples were run in 99.8 atom % D-Chloroform (CDCl3) solvent containing 0.03% TetramethylSilane (TMS).

In the spectra obtained for acylated cellobiose using proton NMR spectroscopy, the alpha and the beta anomeric forms have distinct peaks at distinct chemical shifts. The location of the peaks also depends on whether the anomeric carbon is substituted by hydroxyl or by an acyl group. A doublet at low field is due to the proton on the anomeric carbon of the alpha-anomer (J$_{axial-equal}$=3.8 HZ; 6.26 ppm) when the anomeric carbon has been acylated, whereas the corresponding doublet is at a chemical shift of 5.36 ppm when its substituent is hydroxyl. Correspondingly, the spectrum comprises a set of doublets at a higher field due to the proton on the anomeric carbon of the beta anomer (J$_{axial-axial}$ 7.9 HZ; 5.65 ppm) when the anomeric carbon is acylated and at a chemical shift of 4.82 ppm when the anomeric carbon is merely hydroxyl substituted. A linear comparison of the peak areas enables the relative proportions of the two anomers to be determined.

The ability of proton NMR spectroscopy to distinguish between acylated cellobiose molecules in which the cellobiose anomeric carbon is substituted by an hydroxyl or acyl group can be enhanced by employing a method in which the spectrum of the as-made sample is taken, the hydroxyl group in the sample is reacted with trichloroacetyl isocyanate (TCAI) and the spectrum of the sample is taken again. The chemical shift for TCAI-adducted alpha molecule is 6.33 ppm and for TCAI-adducted beta molecule is 5.73 ppm. By comparing the peak areas of the spectra, the relative proportions of the alpha plus beta hydroxyl, alpha acylated, and beta acylated molecules can be determined.

TABLE 1

| Ex No | Ester substituent | Route | α, β ratio | % Y | MP (° C.) |
|---|---|---|---|---|---|
| 1.1 | Benzoyl | 3A | 2% α, 98% β | 97 | 68 |
| 1.2 | Benzoyl | 3B | 96% α, 4% β | 100 | 85 |
| 1.3 | 2-Naphthoyl | 3A | 1% α, 99% β | 100 | 84 |
| 1.4 | 2-Naphthoyl | 3B | 99% α, 1% β | 100 | 85 |
| 1.5 | Ethanoyl | 3C | 33% α, 67% β | 98 | 68 |
| 1.6 | Ethanoyl | 3A | 62% α, 38% β | 99 | 87 |
| 1.7 | Ethanoyl | 3B | 92% α, 8% β | 79 | 92 |
| 1.8 | n-Hexadecanoyl | 3A | 16% α, 84% β | 97 | 50 |
| 1.9 | n-Hexadecanoyl | 3B | 98% α, 2% β | 100 | 55 |
| 1.10 | Cyclohexanoyl | 3A | 3% α, 97% β | 100 | 79 |
| 1.11 | Cyclohexanoyl | 3B | 89% α, 11% β | 97 | 70 |
| 1.12 | Cyclohexanoyl | 3A | 4% α, 96% β | 98 | 78 |
| 1.13 | Cyclohexanoyl | 3A | 8% α, 92% β | 100 | 79 |
| 1.14 | Cyclohexanoyl | 3A | 8% α, 92% β | 95 | 77 |
| 1.15 | Biphenoyl | 3A | 3% α, 97% β | 100 | 84 |
| 1.16 | n-Propanoyl | 3C | 54% α, 46% β | 100 | 84 |
| 1.17 | n-Propanoyl | 3A | 41% α, 59% β | 99 | 83 |
| 1.18 | n-Butanoyl | 3A | 18% α, 82% β | 100 | 84 |
| 1.19 | n-Butanoyl | 3B | 95% α, 5% β | 98 | 92 |
| 1.20 | n-Pentanoyl | 3A | 38% α, 62% β | 100 | 81 |
| 1.21 | n-Hexanoyl | 3A | 13% α, 87% β | 100 | 87 |
| 1.22 | n-Heptanoyl | 3A | 18% α, 82% β | 100 | 86 |
| 1.23 | n-Dodecanoyl | 3A | 26% α, 74% β | 100 | 78 |
| 1.24 | n-Tetradecanoyl | 3A | 39% α, 61% β | 100 | 71 |
| 1.25 | Cyclohexane ethanoyl | 3A | 5% α, 95% β | 97 | 80 |

EXAMPLE 2

In this Example, cellobiose heptadecanoate esters are prepared using the routes described for Example 1, but employing decanoic acid instead of nonanoic acid in step 1. The results are summarised in Table 2 below.

TABLE 2

| Ex No | Ester substituent | Route | α, β ratio | % Y | MP (° C.) |
|---|---|---|---|---|---|
| 2.1 | Benzoyl | 3A | 4% α, 96% β | 100 | 79 |
| 2.2 | Benzoyl | 3B | 82% α, 18% β | 93 | 85 |
| 2.3 | Ethanoyl | 3C | 38% α, 62% β | 94 | 77 |
| 2.4 | Ethanoyl | 3A | 59% α, 41% β | 98 | 87 |
| 2.5 | Ethanoyl | 3B | 95% α, 5% β | 86 | 102 |
| 2.6 | Benzoyl | 3A | 5% α, 95% β | 100 | 85 |
| 2.7 | 2-Naphthoyl | 3A | 3% α, 97% β | 100 | 84 |
| 2.8 | 2-Naphthoyl | 3B | 94% α, 6% β | 100 | 80 |
| 2.9 | 4-Biphenoyl | 3A | 8% α, 92% β | 100 | 82 |
| 2.10 | Cyclohexanoyl | 3A | 5% α, 95% β | 99 | 77 |
| 2.11 | Hexanoyl | 3A | 28% α, 72% β | 100 | 80 |
| 2.12 | n-Hexadecanoyl | 3A | 17% α, 83% β | 100 | 65 |
| 2.13 | n-Hexadecanoyl | 3B | 97% α, 3% β | 100 | 52 |

Cellobiose octanonanoate, cellobiose octadecanoate and cellobiose heptanonaoate reference materials, which are employed in Examples 5 to 17 hereinbelow.

TABLE 3

| Ref | Acyl Groups | α, β ratio | % Y | MP (° C.) |
|---|---|---|---|---|
| REF 1 | Nonanoyl | 100% α, | 100 | 97 |
| REF 2 | Nonanoyl | 88% α, 12% β | 98 | 80 |
| REF 3 | Nonanoyl | 1% α, 99% β | 100 | 80 |
| REF 4 | Decanoyl | 85% α, 15% β | 84 | 85 |
| REF 5 | Nonanoyl | 50% α, 50% β | 0 | 114 |
| REF 6 | Decanoyl | 50% α, 50% β | 0 | 105 |

EXAMPLE 3

In this Example, further esters were made comprising cellobiose heptanonanoate and a different ester group at the anomeric position. The process comprised a variation of the three stage process described in Example 1 above, the principal differences being indicated herein.

In stage 1, a base catalyst was employed, producing β-D-cellobiose octanonanoate.

D-(+)cellobiose (ACROS; 99% HPLC; 67% β anomer), nonanoyl acid chloride (83 g, 0.47 mol), 96% ALDRICH, (assay; GC: 97.4% with remainder of 2-methyloctanoyl chloride); dry chloroform 99+% (Sure Seal™ bottle, reagent grade, ALDRICH), dry pyridine 99.8+% (sure seal bottle, reagent grade ALDRICH), tetrahydrofuran (Fisher, reagent grade) and methanol (FISHER, reagent grade) were used as received.

A 250 ml three round bottom flask was fitted with a double surface condenser, a pressure equalising funnel and an over head stirrer. All glassware had previously been dried over night at 105° C.

Clear, very faintly yellow nonanoyl chloride (83.2 g, 0.47 mol) was added dropwise slowly, taking between 15 and 30 minutes with constant stirring to a solution of cellobiose (10 g, 0.029 mol) in dry chloroform (40 mls) and dry pyridine (20 mls) at 50° C. The resultant heterogeneous pale yellow mixture was allowed to react for at 50° C. under inert atmosphere and vigorous stirring until monitoring via proton NMR and HPLC indicated that no hepta-substituted cellobiose was present, a period of about 20 hours.

The heterogeneous light yellow mixture was cooled down to room temperature. Then, the reaction mixture was poured into methanol (1000 mls) and stirred for about 15 minutes, producing a precipitate which was recoved by filtration, washed with 50 mls fresh methanol and dried in a vacuum oven (0.8 mbar, 80 Pa) at 40 to 45° C. for 5 hours, 39 g of a white solid was recovered.

The white solid was recrystallised three times from a tetrahydrofuran/methanol mixture (75/200 mls), filtered, washed with 50 ml of methanol and dried in a vacuum oven for 5 hours at 40–45° C. 18 g of a white solid (42%) was obtained.

In stage 2, the process of stage 2 of Example 1 was repeated, but on a $1/5^{th}$ scale. The reaction mixture was maintained at 40° C. for a total of 7 hours. The recovered recrystallised precipitate was dried in a vacuum oven at 40° C. for between 5 and 6 hours under a pressure between 0.8 to 1.0 mbar (80 to 100 Pa).

In Stage 3, the process of stage 3A of Example 1 was repeated, except that the triethylamine and the acyl chloride were each employed at a mole ratio of 2.5:1 to the cellobiose heptanonanoate. The recovered recrystallised precipitate was dried in a vacuum oven at 40° C. for between 5 and 6 hours under a pressure between 0.8 to 1.0 mbar.

The extent of acylation, and proportion of α and β anomers were measured as in Example 1, and the results summarised in Table 4 below.

TABLE 4

| Ex No | Ester substituent | α, β ratio | % Y | MP (° C.) |
|---|---|---|---|---|
| 3.1 | Cyclohexanoyl | 19% α, 81% β | 100% | 75 |
| 3.2 | Cyclohexanoyl | 6% α, 94% β | 99.5% | 76 |
| 3.3 | Cyclohexanoyl | 2% α, 98% β | 100% | ~85 |
| 3.4 | 2-Ethylhexanoyl | 2% α, 98% β | 100% | 72 |
| 3.5 | Cyclopentanoyl | 40% α, 60% β | 100% | 79 |
| 3.6 | 6-Acetamidohexanoyl | | | |

EXAMPLE 4

In this Example, various samples of esterified cellobiose prepared as in Example 1 or 2 above, were used to gel water-immiscible cosmetic liquids, in accordance with the procedure given below, in which a large number of gels can be prepared simultaneously.

The samples were tested in a 96 well (8×12 rows) glass micro-titre plate. Each well had a volume of about 1 ml. About 0.01 or 0.02 g of each esterified cellobiose material was placed into 8 consecutive wells in a single row, so that each well contained approximately 5% or 10% of the cellobiose ester. The balance in each well comprised the cosmetic liquid by addition of approximately 0.2 g of the respective liquid to each cell. A glass lid was placed on top of the plate. The plate was carefully placed in a thermostatically controlled fan-assisted oven set at 150° C. for 2.5 hours. The plate was removed from the oven and allowed to cool naturally to ambient laboratory temperature. The contents of the wells were assessed at the end of the cooling period, by visual inspection and by poking the contents of each well with a micro-spatula. The plates were stored at 18° C. for 18 hours and the contents inspected, and further stored for 18 hours at 4° C. and inspected for a third time. The results obtained in the tests are summarised in Table 5 below, in which the legend is as follows:

| | |
|---|---|
| gel | gel |
| g4 | gel after overnight (18 hrs) storage at 4° C. |
| g22 | gel after overnight (18 hrs) storage at 22° C. |
| sg | soft gel |
| sg22 | soft gel after overnight (18 hrs) storage at 22° C. |
| sol | solution |
| * | the test at 4° C. was not carried out |

TABLE 5

| Product of Ex | 1.1 | | 1.2 | | 1.3 | | 1.4 | | 1.5 | | 1.6 | | 1.7 | | 1.8 | | 1.9 | |
|---|---|---|---|---|---|---|---|---|---|---|---|---|---|---|---|---|---|---|
| Weight % | 5% | 10% | 5% | 10% | 5% | 10% | 5% | 10% | 5% | 10% | 5% | 10% | 5% | 10% | 5% | 10% | 5% | 10% |
| ISA | g22 | gel | sg | gel | gel | gel | g22 | g22 | g22 | gel | sg | gel | sg | gel | g22 | g22 | g22 | g22 |
| IPM | g4 | gel | sol | sol | g4 | g22 | sol | sol | | | | | | | | | g4 | g4 |
| Mineral oil | gel | gel | sg | gel | g22 | g22 | g22 | g22 | g22 | gel | sg | gel | sg | gel | g22 | g22 | g22 | g22 |
| Finsolv TN | g4 | gel | sol | sol | sol | g4 | sol | sol | | | | | | | | | | |
| Fluid AP | gel | gel | sg | gel | gel | gel | gel | gel | gel | gel | sg | gel | gel | gel | gel | gel | gel | gel |
| Polydecene | gel | gel | gel | gel | gel | gel | g22 | gel | gel | gel | gel | gel | gel | gel | gel | gel | gel | gel |
| DC556 | gel | gel | gel | gel | gel | gel | gel | gel | g22 | gel | sg22 | gel | gel | gel | gel | gel | gel | gel |

| Product of Ex | 1.10 | | 1.11 | | 1.14 | | 1.15 | | 1.16 | | 1.18 | | 1.20 | | 1.21 | | 1.22 | |
|---|---|---|---|---|---|---|---|---|---|---|---|---|---|---|---|---|---|---|
| Weight % | 5% | 10% | 5% | 10% | 5% | 10% | 5% | 10% | 5% | 10% | 5% | 10% | 5% | 10% | 5% | 10% | 5% | 10% |
| ISA | g22 | gel | g22 | g22 | g22 | gel | gel | gel | gel | gel | sg22 | gel | sg22 | g22 | sg22 | g22 | sg22 | g22 |
| IPM | sol | g4 | sol | sol | sol | g4 | | | | | | | | | | | | |
| Mineral oil | gel | gel | g22 | g22 | gel | gel | gel | gel | gel | gel | g22 | gel | g22 | gel | g22 | gel | sol | g22 |
| Fluid AP | gel | gel | gel | gel | gel | gel | gel | gel | gel | gel | gel | gel | g22 | gel | gel | gel | gel | gel |
| Polydecene | gel | gel | gel | gel | gel | gel | gel | gel | gel | gel | gel | gel | gel | gel | gel | gel | gel | gel |
| DC556 | gel | gel | g22 | gel | gel | gel | gel | gel | gel | gel | gel | gel | g22 | g22 | g22 | gel | g22 | g22 |

| Product of Ex | 1.23 | | 1.24 | | 1.25 | | 2.1 | | 2.2 | | 2.3 | | 2.4 | | 2.5 | | 2.7 | |
|---|---|---|---|---|---|---|---|---|---|---|---|---|---|---|---|---|---|---|
| Weight % | 5% | 10% | 5% | 10% | 5% | 10% | 5% | 10% | 5% | 10% | 5% | 10% | 5% | 10% | 5% | 10% | 5% | 10% |
| ISA | g22 | g22 | g22 | gel | g22 | g22 | gel | gel | gel | gel | gel | gel | gel | gel | gel | gel | gel | gel |
| Mineral oil | g22 | g22 | g22 | g22 | gel | gel | gel | gel | gel | gel | gel | gel | gel | gel | gel | gel | gel | gel |
| Fluid AP | sg | gel | gel | gel | gel | gel | gel | gel | gel | gel | gel | gel | gel | gel | gel | gel | gel | gel |
| Polydecene | gel | gel | gel | gel | gel | gel | gel | gel | gel | gel | gel | gel | gel | gel | gel | gel | gel | gel |
| DC556 | gel | gel | gel | gel | g22 | gel | gel | gel | gel | gel | gel | gel | gel | gel | gel | gel | gel | gel |

| Product of Ex | 2.9 | | 2.10 | | 2.11 | | 2.12 | | 2.13 | | 3.5 | |
|---|---|---|---|---|---|---|---|---|---|---|---|---|
| Weight % | 5% | 10% | 5% | 10% | 5% | 10% | 5% | 10% | 5% | 10% | 5% | 10% |
| ISA | g22 | gel | g22 | gel | gel | gel | g22 | gel | gel | gel | sg22 | g22 |
| Mineral oil | sg | gel | gel | gel | gel | gel | gel | gel | gel | gel | sol* | gel |
| Fluid AP | gel | gel | gel | gel | gel | gel | gel | gel | gel | gel | sg22 | gel |
| Polydecene | gel | gel | gel | gel | gel | gel | gel | gel | gel | gel | gel | gel |
| DC556 | gel | gel | gel | gel | gel | gel | gel | gel | gel | gel | g22 | gel |

From Table 5, it can be seen that the CHME esters were particularly suited to gelling silicone oils, hydrocarbon oils, ethers and liquid fatty alcohols.

EXAMPLE 5

In this Example the Fibre dissolution temperature (FDT) is measured in the DSC process described later herein, by observing when the fibres dissolve whilst the temperature of sample rises. FDT is taken to be the peak temperature of the highest peak.

The results are summarised in Table 6 below in which Anomeric description indicates the α:β ratio and the acyl substituent at the anomeric carbon. In REF2 and REF3, the acyl substituents at the other seven cellobiose sites are nonanoyl.

TABLE 6

| Code | Product of | Anomeric Description | FDT (° C.) | Solubility of structurant at 25° C. |
|---|---|---|---|---|
| REF 2 | | nonanoyl, 88% α | 47 | Benchmark. Some dissolution of structurant clearly seen in DSC |
| REF 3 | | nonanoyl, 99% β | 47 | Slightly less soluble than benchmark. Some dissolution of structurant seen in DSC |
| Ex 5.1 | Ex 1.1 | benzoyl, 98% β | 64 | Less soluble. No dissolution of fibres seen in DSC |
| Ex 5.2 | Ex 1.2 | benzoyl, 96% α | 67 | Less soluble. No dissolution of fibres seen in DSC |
| Ex 5.3 | Ex 1.3 | naphthoyl, 99% β | 63 | Less soluble. No dissolution of fibres seen in DSC |
| Ex 5.4 | Ex 1.5 | ethanoyl, 33% α | 50 | Less soluble. No dissolution of fibres seen in DSC |
| Ex 5.5 | Ex 1.6 | ethanoyl, 62% α | 70 | Less soluble. No dissolution of fibres seen in DSC |
| Ex 5.6 | Ex 1.7 | ethanoyl, 92% α | 72 | Less soluble. No dissolution of fibres seen in DSC |
| Ex 5.7 | Ex 1.10 | cyclohexanoyl, 97% β | 53 | Less soluble. No dissolution of fibres seen in DSC |

From Table 6, two deductions can be made. First, the fibre dissolution temperature of the structurants according to the instant invention are higher than the reference structurants, indicating that the thermal stability (stability to melting) of a gel obtained using that invention structurant is higher.

Secondly, the solubility of the invention structurants at 25° C. tends to be lower than that of the reference structurants. The inventors have found such lower solubility indicates that the resistance of the structurant to crystallisation during storage of gels is improved.

DSC Method

Samples of gel (about 20 mg) were sealed in stainless steel capsules for DSC. An empty stainless steel capsule was used as the physical reference. The samples were subjected to the following temperature programme:

The sample was heated to 100° C. and held at 100° C. for 1 minute, in order to obtain an isotropic solution. The sample was then cooled at 5 K/min to −20° C. The sample was held at −20° C. for 1 minute. The sample is now a gel on the bottom of the sample capsule prepared in a reproducible manner. The gel was then heated at 5 K/min to 100° C. Data was also obtained with empty stainless steel pans as both physical sample and reference. This blank data was later subtracted from the sample data to remove any curvature in the base line.

EXAMPLE 6

Stability Testing

Gels were made up using 10% structurant in a 60:40 mixture of Hydrogenated Polyisobutene (Panalene L14E) :DC245. The gels, in sealed glass bottles, were left to stand for 18 hrs at room temperature, after which they were transferred to an oven thermostatically controlled to 37° C. Samples were checked periodically for signs of crystal growth visible by eye. REF1 is cellobiose octanonanoate. The results are summarised in Table 7 below.

TABLE 7

| Structurant | Observation |
|---|---|
| REF 1 | Small crystals visible in gel after 18 hrs at RT. More and bigger crystals after 6 hrs at 37° C. Crystals throughout gel after 3 days at 37° C. |
| REF 2 | Slight loss of clarity after 7 days at 37° C. Fine crystals on surface after 8 days at 37° C. Fine needle crystals throughout gel after 9 days at 37° C. More needle crystals in gel bulk and crystal mass on surface after 13 days at 37° C. Large amount of crystals throughout gel after 17 days at 37° C. |
| Product of Ex 1.7 | No crystals after 17 days. |
| Product of Ex 1.2 | No crystals after 17 days. |
| Product of Ex 1.10 | No crystals after 17 days. |

Table 7 shows that there is a distinct advantage for the invention structurants over both REF1 and REF2 in terms of resistance to crystallisation during storage.

EXAMPLE 7

This Example shows some benefits obtainable by employing a fraction of a structurant in accordance with the present invention in conjunction with a structurant exemplified or described in PCT/GB 00/01228.

In this Example, 60:40 hydrogenated polydecene:DC245 was gelled with a combination of 9% cellobiose octanonanoate (87.5% α, code REF2) and 1% of the specified cellobiose ester. The transparency and light transmission of the samples are summarised in Table 8, in which % T is the % light transmitted at a wavelength of 580 nm.

TABLE 8

| | Anomeric | Clarity | |
|---|---|---|---|
| Code | Description | Visual | % T |
| REF 2 | nonanoyl, 87.5% α | transparent/slight haze 5 | 41 |
| REF 3 | nonanoyl, 99% β | transparent/translucent 4 | 46 |
| REF 5 | hydroxy, 50% α | transparent/translucent 4 | 31 |

TABLE 8-continued

|  | Code | Anomeric Description | Clarity Visual | % T |
|---|---|---|---|---|
| Ex 7.1 | Ex 1.1 | benzoyl, 98% β | transparent/translucent 5 | 55 |
| Ex 7.2 | Ex 1.2 | benzoyl, 96% α | transparent/translucent 4 | 38 |
| Ex 7.3 | Ex 1.3 | naphthoyl, 99% β | transparent 4 | 58 |
| Ex 7.4 | Ex 1.4 | naphthoyl, 99% α | transparent/slight haze >8 | 38 |
| Ex 7.5 | Ex 1.5 | ethanoyl, 33% α | transparent >8 | 49 |
| Ex 7.6 | Ex 1.6 | ethanoyl, 62% α | transparent >8 | 49 |
| Ex 7.7 | Ex 1.7 | ethanoyl, 92% α | transparent >8 | 52 |
| Ex 7.8 | Ex 1.9 | hexadecanoyl, 98% α | transparent >8 | 45 |
| Ex 7.9 | Ex 1.10 | cyclohexanoyl, 97% α | transparent/slight haze 6 | 42 |

From Table 8, it can be seen that the addition of the invention structurants tended to produce a gel that was visually a little better in that the panel score was higher than when the reference structurants were added. This is confirmed by the % T data, light transmission, which similarly showed a similar and for most, a higher light transmission.

Visual assessment score

A gel contained within a 1 cm thick cuvette was placed directly on to a sheet of white paper on which 21 sets of figures where printed in black. The size and thickness of the figures varied systematically and were numbered from −12 (the largest, thickest set) through 0 to 8 (the smallest thinnest set) The score given to each gel was the highest numbered set which could be read clearly through the gel, the higher the number, the higher the clarity.

Light transmission

The translucency of a composition may be measured by placing a sample of standardised thickness in the light path of a spectrophotometer and measuring transmittance, as a percentage of light transmitted in the absence of the gel.

This test was carried out using a dual-beam spectrophotometer. The sample of composition was poured hot into a 4.5 ml cuvette made of poly(methyl-methacrylate) (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittence measured at any temperature in the range from 20–25° C. is usually adequately accurate, but measurement is made at 22° C. if more precision is required.

EXAMPLE 8

In this Example, the fibre dissolution temperature, the % light transmission and visual clarity assessments were made in respect of cellobiose heptanonanoate monocyclohexanoate made in Example 1 or 3, using the methods described in Examples 5 and 7. The gels were prepared in a 60:40 w/w mixture of hydrogenated polydecene:volatile silicone (Silkflo 364:DC245). The results are summarised in Table 9 below.

TABLE 9

| Product of Ex No | % β | % Y | FDT (° C.) | % T | Visual |
|---|---|---|---|---|---|
| 1.10 | 97% | 100% | 53 | 48 | >8 |
| 1.12 | 96% | 98% | 51 | 38 | 3 |
| 1.13 | 92% | 100% | 52 | 41 | 6 |
| 1.14 | 92% | 95% | 49 | 22 | 3 |
| 3.1 | 81% | 99.5% | 48 | 26 | 3 |
| 3.2 | 94% | 100% | 49 | 34 | 5 |
| 3.3 | 98% | 100% | 53 | 53 | >8 |

EXAMPLE 9

In this Example, the procedure of Example 7 was followed, but employing 9% REF4 to which was added 1% of itself or the other reference or invention material. The gels were tested in the same manner as in Example 7 and the results summarised in Table 10 below.

TABLE 10

| Ex No | Product of Ex | Anomeric Description | Clarity Visual | % T |
|---|---|---|---|---|
| REF 4 |  | decanoyl, 85% α | opaque <−12 | 0.36 |
| REF 6 |  | hydroxyl, 50% α | opaque <−12 | 0.8 |
| Ex 9.1 | 2.1 | benzoyl, 96% β | translucent −1 | 9.53 |
| Ex 9.2 | 2.6 | benzoyl, 95% β | translucent −8 | 4.5 |
| Ex 9.3 | 2.7 | naphthoyl, 97% β | translucent 0 | 8.7 |
| Ex 9.4 | 2.9 | 4-biphenoyl, 92% β | translucent −3 | 7.7 |
| Ex 9.5 | 2.10 | cyclohexanoyl, 95% β | translucent −5 | 5.9 |

From Table 10, it can be seen that the addition of the invention structurants tended to produce a gel that was visually much better in that the visual assessment was higher than when the reference structurants were added. This is confirmed by the % T data, light transmission, which similarly showed a much higher light transmission.

EXAMPLE 10

In this Examples, gels are prepared as in Example 9, but employing various weight ratios of ACB structurant REF4 and the invention ester produced in Example 2.6 to a total weight of 10% in a 60:40 w/w mixture of hydrogenated polydecene:volatile silicone (Silkflo 364NF:DC245). The results are summarised in Table 11 below.

TABLE 11

| Ex No | Weight ratio Ex 2.6:REF 4 | Clarity Visual Score | % T |
|---|---|---|---|
| 10.1 | 10:0 | <−12 | 0.15 |
| 10.2 | 7:3 | <−12 | 0.51 |
| 10.3 | 5:5 | <−12 | 0.65 |
| 10.4 | 4:6 | −4 | 7.0 |
| 10.5 | 3:7 | 5 | 17.9 |
| 10.6 | 2:8 | 3 | 14.0 |
| 10.7 | 1:9 | −8 | 4.5 |
|  | 0:10 | <−12 | 0.36 |

From Table 11, it can be seen that the clarity of the gels comprising a mixture of CHME (invention) ester and the reference product were superior to the gel employing solely the invention ester or the reference product REF4. The best clarity was achieved when an excess proportion of the ACB structurant ester was employed, and particularly in the ratio range for CHME: ACB of 35:65 to 15:85.

EXAMPLE 11

In this Example, Example 10 was repeated, but employing reference ester REF2 and a CHME ester, the product of Ex 1.12 or Ex 1.13. The results are summarised in Table 12 below.

TABLE 12

| Ex No | Weight ratio CHME:REF2 | % T Ex 1.12 | Ex 1.13 |
|---|---|---|---|
| 11.1 | 10:0 | 37.7 | 41.0 |
| 11.2 | 7:3 | 38.7 | 29.1 |
| 11.3 | 5:5 | 10.3 | 16.1 |
| 11.4 | 4:6 | 12.6 | 12.1 |
| 11.5 | 3:7 | 51.1 | 50.6 |
| 11.6 | 2:8 | 53.6 | 50.5 |
| 11.7 | 1:9 | 34.7 | 40.3 |
|  | 0:10 | 41 | 41 |

From Table 11, it can be seen that even when the reference (ACB) ester provided a translucent gel, it was possible to select combinations of the CHME and ACB esters which gave improved clarity, and particularly in the eight ratio range of from 35:65 to 15:85 of CHME:ACB esters.

EXAMPLE 12

Gels were made up and tested in accordance with the procedure in Example 6, as such or modified by employing a weight ratio of 9% of REF1 and 1% of an additional structurant as specified in Table 13 below.

TABLE 13

| Structurant | Observations |
|---|---|
| solely REF1 | Small crystals visible in gel after 18 hrs at RT. More and bigger crystals after 6 hrs at 37° C.; Crystals throughout gel after 3 days at 37° C. |
| + REF3 | Some crystal growth on gel surface after 1 day at 37° C. Much more crystallisation at surface and needle shaped crystals in bulk gel after 6 days at 37° C. Crystals throughout gel after 9 days at 37° C.; More crystals throughout gel after 13 days at 37° C. |
| + product of Ex 1.1 | Slight crystal growth on surface after 11 days at 37° C. |
| + product of Ex 1.3, | No crystals after 12 days at 37° C. |
| + product of Ex 1.7 | Slight crystal growth on surface after 13 days at 37° C. |
| + product of Ex 1.8 | No crystals after 15 days at 37° C. |
| + product of Ex 1.10 | No crystal growth after 12 days at 37° C. |

Table 13 shows that there is significant improvement in stability as a result of adding a proportion of the structurant of the instant invention to the structurant of PCT/GB 00/01228. Likewise, there is a benefit for adding the invention products compared with adding reference product REF3 to the structurant of PCT/GB 00/01228.

EXAMPLE 13

The test procedure of Example 9 was repeated, but using ACB structurant REF2 alone as the structurant or to which a CHME structurant was added. The results are summarised in Table 14 below.

TABLE 14

| Structurant | Observation |
|---|---|
| solely REF2 | Slight loss of clarity after 7 days at 37° C. Fine crystals on surface after 8 days at 37° C. Fine needle crystals throughout gel after 9 days at 37° C. More needle crystals in gel bulk and crystal mass on surface after 13 days at 37° C. |
| + product of Ex 1.1 | No crystals after 12 days at 37° C. |
| + product of Ex 1.3 | No crystals after 12 days at 37° C. |
| + product of Ex 1.7 | Slight very fine crystal growth after 13 days at 37° C. |
| + product of Ex 1.10 | Some needle crystals on surface after 11 days at 37° C. Some needle crystals in gel bulk after 12 days at 37° C. |

From Table 14, it can be seen that the addition of the invention structurants to reference structurant REF2 according to PCT/GB 00/1228 improves the resistance of the structurant to crystallisation during storage.

EXAMPLE 14

An antiperspirant suspension stick was prepared using a water-immiscible liquid or a mixture of water-immiscible liquids, an antiperspirant active and an esterified cellobiose. The procedure was as follows:

the mixture of liquids was heated to a temperature 5 to 10° C. above a temperature at which the esterified cellobiose had been observed to dissolve in a preliminary test. During this heating the liquid was mixed gently using a Silverson mixer. The esterified cellobiose was added and allowed to dissolve. Next, the particulate antiperspirant active was added to this solution. The resulting mixture was then allowed to cool (or, if necessary, heated) whilst mixing gently until it reached a temperature of about 5 to 10° C. above the gelling point. At this stage the mixture was poured into antiperspirant stick barrels and left to cool without further disturbance until the formulation had solidified.

The resulting sticks were evaluated after at least 24 hours at ambient laboratory temperature, the appearance of the stick was noted, the hardness was determined by penetrometer, and tests of deposition and whiteness of the resulting deposit were carried out using the procedures described hereinafter. The results are summarised in Table 15 below.

The materials employed in the formulations in this and subsequent Examples are as follows:

| Code | Description | Trademark |
|---|---|---|
| AZAG | Al/Zr Tetrachlorohydrex glycine complex | Reach 908 |
| AACH | Activated aluminium chlorohydrate hydrated to RI of 1.508 | Aloxicoll LR (hydrated) |
| ACHaq | 50% aqueous aluminium chlorohydrate solution | Zirconal 50 |
| Car1 | Hydrogenated Polydecene | Silkflo 364NF |
| Car2 | Volatile silicone blend | DC245 |
| Car3 | Octyldodecanol | Eutanol G |

-continued

| Code | Description | Trademark |
|---|---|---|
| Car4 | Mineral Oil | Sirius M70 |
| Car5 | 1,1,5,5-tetraphenyltrisiloxane | DC704 |
| Glycerol | Moisturiser - glycerol | |
| Emulsifier | Dimethicone copolyol emulsifier | Abil EM90 |
| REFNo | Reference ACB ester as in Table 3 | |
| ExNo | CHME Ester prepared in specified Example number | |

TABLE 15

| Constituent | % w/w |
|---|---|
| AZAG - Al/Zr Tetrachlorohydrex glycine complex | 24.0 |
| Car1 - Silkflo 364NF | 13.8 |
| Car2 - DC245 (volatile silicone) | 55.2 |
| REF1 - (Cellobiose octanonanoate) | 6.3 |
| CHME Ester prepared in Ex 1.7 | 0.7 |
| Properties | |
| Penetrometer Hardness (mm) | 14.6 |
| Deposition on black wool after 24 hours | 33 |

From Table 15, it can be seen that a suspension stick with suitable hardness and low visible deposition can be made using a combination of the ACB cellobiose structurant according to PCT/GB 00/01228 and the CHME invention structurant.

Further suspension sticks having acceptable hardness and low visible deposits can be made by substituting the structurant made in each of Examples 1.1 to 1.6 or 1.8 to 1.11 for that made in Ex 1.7 or for the combined weight of REF1 plus that of Ex 1.1 in the above formulation or similarly for 2.1 to 2.5 in combination with REF4 instead of REF1.

EXAMPLE 15

In this Example further suspension sticks were made by the process of Example 14, to prepare sticks containing various carrier fluids CHME esters made in the specified earlier Example, alone or with reference structurant REF4 as summarised in Table 16 below. The hardness is a penentrometer hardness and the deposit is the measured deposition on black woll after 24 hours.

TABLE 16

| | Example No | | | |
|---|---|---|---|---|
| | 15.1 | 15.2 | 15.3 | 15.4 |
| | % w/w | | | |
| Constituent | | | | |
| AZAG | 24 | 24 | | |
| AACH | | | 25 | 25 |
| Car1 | 13.8 | | 26.84 | 26.04 |
| Car2 | 52.2 | 52 | | |
| Car3 | | 4 | | |
| Car4 | | 10 | | |
| Car5 | | | 40.16 | 38.96 |
| REF4 | | 7 | | |

TABLE 16-continued

| | Example No | | | |
|---|---|---|---|---|
| | 15.1 | 15.2 | 15.3 | 15.4 |
| | % w/w | | | |
| Ex 2.9 | | 3 | | |
| Ex 1.12 | 10 | | | |
| Ex 1.15 | | | 8 | |
| Ex 1.3 | | | | 10 |
| Properties | | | | |
| Hardness mm | 13.4 | 11.8 | 21.3 | ND |
| Deposit | 37 | ND | ND | ND |
| Visual Appearance | Opaque | Opaque | Translucent | Translucent |

EXAMPLE 16

In this Example, an emulsion stick was prepared by mixing cyclomethicone with the other organic liquids including the cetyl dimethicone copolyol which functioned as an emulsifier (silicone surfactant) and the mixture was heated with gentle stirring to a temperature 5 to 10° C. above the temperature at which the structurant had been found to dissolve. The esterified cellobiose was then added and allowed to dissolve.

The disperse phase (also referred to as internal phase) was an aluminium zirconium active dissolved in water or in a mixture of a polyol and water. This disperse phase was pre-heated to the same temperature as the organic oils containing the esterified cellobiose and added slowly to them over a period of one minute while mixing with a Silverson mixer. After addition was complete the formulation was mixed at higher speed for five minutes. Stirring speed was then reduced for a further one minute after which the mixture was poured into stick barrels and allowed to cool undisturbed to ambient laboratory temperature. The sticks were tested by penetrometer, and for whiteness of deposits, in each instance by the test procedures given earlier. The results are summarised in Table 17 below.

TABLE 17

| Constituent | % w/w |
|---|---|
| ACHaq - Zirconal 50 | 40.0 |
| Glycerol | 10.0 |
| Car1 - Silkflo 364NF | 25.52 |
| Car2 - DC245 | 18.48 |
| ABIL EM90 (emulsifier) | 1 |
| Ester prepared in Ex 1.10 | 5.0 |
| Properties | |
| Penetrometer Hardness (mm) | 17.1 |
| Deposition on black wool after 24 hours | 17 |
| % Light Transmission at 580 nm at 19° C. | 34 |

From Table 17, it can be seen that the emulsion stick produced according to Example 11 had acceptable hardness and particularly low visible deposits and has high visual clarity.

Further emulsion sticks having acceptable hardness and low visible deposits are made by substituting the structurant made in each of Examples 1.1 to 1.9 or 1.11 or 2.1 to 2.5 for that made in Ex 1.10 or by substituting up to 90% of the weight of the structurant by REF1 or REF2 or REF4 described hereinabove.

EXAMPLE 17

In this Example, further emulsion sticks were prepared by the method of Example 16, with the compositions, rounded to 1 decimal place and properties as summarised in Table 18 below. The melt characteristics and the crystallisation stability of many of the sticks were also measured and are summarised in Table 20 below. The description of any crystals visible under an intense light source relates to the specified period at which the stick was translucent.

TABLE 18

| | Example No | | | | | |
|---|---|---|---|---|---|---|
| | 17.1 | 17.2 | 17.3 | 17.4 | 17.5 | 17.6 |
| | % w/w | | | | | |
| Constituent | | | | | | |
| ACHaq | 38.9 | 38.9 | 38.9 | 40 | 39.2 | 39.2 |
| Car1 | 25.2 | 25.2 | 23.7 | | 26.1 | 25.2 |
| Car2 | 16.8 | 16.8 | 15.8 | 19.6 | 17.4 | 17.0 |
| Car4 | | | | 19.9 | | |
| Glycerol | 11.1 | 11.1 | 11.1 | 10 | 11.1 | 11.1 |
| Emulsifier | 0.5 | 0.5 | 0.5 | 0.5 | 0.5 | 0.5 |
| Ex 1.22 | 7.5 | | | | | |
| Ex 1.24 | | 7.5 | | | | |
| Ex 2.7 | | | 3 | | | |
| Ex 2.9 | | | | 3 | | |
| REF4 | | | 7 | 7 | | |
| Ex 1.12 | | | | | | 7 |
| Ex 1.13 | | | | | 5 | |
| Perfume | | | | | 1 | |
| Properties | | | | | | |
| Hardness mm | 15.4 | 14.9 | 12.1 | 12.6 | 19.7 | 16.3 |
| Deposit | 13 | 13 | 14 | 19 | 21 | 21 |

| | Example No | | | | | |
|---|---|---|---|---|---|---|
| | 17.7 | 17.8 | 17.9 | 17.10 | 17.11 | 17.12 |
| | % w/w | | | | | |
| Constituent | | | | | | |
| ACHaq | 38.9 | 38.9 | 38.5 | 39.2 | 39.2 | 39.2 |
| Car1 | 25.2 | 25.2 | 23.7 | 25.5 | 26.7 | 25.5 |
| Car2 | 15.4 | 15.8 | 14.4 | 17.0 | 17.8 | 17.0 |
| Glycerol | 11.1 | 11.1 | 11.5 | 10.8 | 10.8 | 10.8 |
| Emulsifier | 0.5 | 0.5 | 0.5 | 0.5 | 0.5 | 0.5 |
| Ex 1.14 | 10 | 10 | | 1.4 | | |
| Ex 3.3 | | | 10 | | | |
| REF2 | | | | 5.6 | | |
| Ex 2.6 | | | | | 1.5 | 1.5 |
| REF4 | | | | | 3.5 | 3.5 |
| Perfume | 1 | | 1 | | | |
| Properties | | | | | | |
| Hardness mm | 12.6 | 11.1 | 11.3 | 19.8 | 19.7 | 16.3 |
| Deposits | 18 | 21 | 19 | 21 | 21 | 21 |

Comparison Formulations

Comparison Formulations lacking a CHME ester structurant were made in the same way as Example 17 formulations. their composition and certain of their properties are summarised in Tables 19 and 20 below.

TABLE 19

| | Comp No | | | |
|---|---|---|---|---|
| | 17.C1 | 17.C2 | 17.C3 | 17.C4 |
| | % w/w | | | |
| Constituent | | | | |
| ACHaq | 39.2 | 39.2 | 38.9 | 38.9 |
| Car1 | 26.1 | 25.5 | 23.1 | 23.7 |

TABLE 19-continued

| | Comp No | | | |
|---|---|---|---|---|
| | 17.C1 | 17.C2 | 17.C3 | 17.C4 |
| | % w/w | | | |
| Car2 | 17.4 | 17.0 | 15.4 | 15.8 |
| Glycerol | 10.8 | 10.8 | 11.1 | 11.1 |
| Emulsifier | 0.5 | 0.5 | 0.5 | 0.5 |
| REF2 | 5 | 7 | 10 | 10 |
| Perfume | 1 | | 1 | |
| Properties | | | | |
| Hardness mm | 15.4 | 14.9 | 12.1 | 12.6 |

TABLE 20

| Ex No C No | Stick Melt Test | Crystallisation Stability at 45° C. |
|---|---|---|
| 17.5 | Stable at 45° C. Soft and leaky at 50° C. Totally melted at 55° C. | Translucent after 6 weeks. A few very tiny crystal specs were visible. |
| 17.6 | Stable at 50° C. Totally melted at 55° C. | Translucent after 6 weeks. A few very tiny crystal specs were visible. |
| 17.7 | Stable at 51° C. Totally melted at 53° C. | Translucent after 13 weeks. A few very tiny crystal specs were visible. |
| 17.8 | Stable at 53° C. Totally melted at 55° C. | Translucent after 13 weeks. A few very tiny crystal specs were visible |
| 17.9 | Stable at 54° C. Totally melted at 56° C. | Translucent after 5 weeks. No visible crystals. |
| 17.10 | Stable at 50° C. Slight liquid on top at 55° C., but retained original shape | Formulation was still translucent after 6 weeks. Very slight domain texture was visible. |
| 17.11 | Stable at 50° C. Slight liquid on top at 55° C., but retained original shape | Translucent after 6 weeks. Very slight domain texture was visible. |
| 17.C1 | Stable at 40° C. Soft and slightly leaky at 45° C. Totally melted at 50° C. | Mottled, opaque and leaky after 2 weeks, and had totally collapsed after 3 weeks. |
| 17.C2 | Stable at 45° C. Totally melted at 50° C. | Mottled and opaque after 4 weeks |
| 17.C3 | Stable at 45° C. Soft and leaky at 47° C. Totally melted at 49° C. | Minor mottling and leakage after 2 weeks. Completely mottled and opaque after 3 weeks. |
| 17.C4 | Stable at 47° C. Totally melted at 49° C. | Minor mottling after 3 weeks. Completely mottled and opaque after 4 weeks. |

Side by side comparison of the Example 17 and Comparison 17C formulations shows that the comparison formulations melted at a lower temperature and became opaque and mottled during storage periods at which the invention formulations were still translucent, thereby demonstrating the superior stability of the invention formulations. The crystallisation test does not indicate the maximum period of time for which any of the invention formulations could remain translucent, because it no instance was it continued until an invention stick became opaque.

Measurement of Properties i) Hardness of stick using a penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10"±15". A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition and whiteness of deposit

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrate used was 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biased the stick against the substrate with a standardised force. The apparatus was operated to pass the stick laterally across the substrate eight times. The substrate was carefully removed from the rig and reweighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

iii) Melting of Stick

A sample stick in its conventional open-mouthed dispensing container was placed in a constant temperature chamber that was maintained for a cycle of 48 hours to enable any change in its condition to develop. The temperature was raised by a 2° C. or 5° C. increment before each succeeding cycle. The stick was observed at the end of each cycle, and the temperature noted at which a change in appearance was visible.

iv) Crystallisation Stability at 45° C.

In a test for determining the stability of ester-structured antiperspirant sticks at an elevated temperature, the sample stick was placed in a constant temperature chamber that was maintained at 45° C. The sticks were observed weekly, to determine whether they were still translucent or whether their appearance had altered. An intense light was shone on the sticks and a visual check was made as to whether any crystals or domains were visible. In several instances, the test on a stick was halted if it was still translucent when a similar comparison stick had become opaque, or shortly afterwards.

We claim:

1. An acylated cellobiose satisfying the general formula:

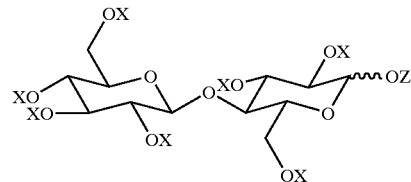

in which X represents an R—CO— group in 6 locations and an acyl group R—CO— or H in a seventh location, Z represents an acyl group R'—CO—, R represents a saturated or unsaturated, linear or branched chain hydrocarbon residue containing from 7 to 11 carbon atoms, and R' represents a residue which is different from R and which is:

(i) a saturated or unsaturated, optionally substituted, linear or branched chain hydrocarbon residue containing from 1 to 31 carbon atoms, where the chain length of R' differs from that of R by at least two carbon atoms or (ii) an aromatic hydrocarbon residue, optionally substituted or (iii) a cycloaliphatic hydrocarbon, optionally substituted.

2. An acylated cellobiose according to claim 1 wherein the R residue is linear.

3. An acylated cellobiose according to claim 1 wherein the R residue comprises 8 or 9 carbons.

4. An acylated cellobiose according to claim 1 wherein the R residue is n-octyl or n-nonyl.

5. An acylated cellobiose according to claim 1 wherein each R residue is the same.

6. An acylated cellobiose according to claim 1 wherein each X represents an R—CO— group.

7. An acylated cellobiose according to claim 6 wherein each R residue is the same.

8. An acylated cellobiose according to claim 1 wherein the R' residue is a residue selected from the group consisting of alkyl residues containing from 1 to 6 or from 11 to 24 carbon atoms, optionally substituted, aromatic residues and cycloaliphatic residues.

9. An acylated cellobiose according to claim 8 wherein the R' alkyl residue is a linear alkyl residue.

10. An acylated cellobiose according to claim 9 wherein the R' aromatic residue comprises a phenyl, naphthyl or biphenyl residue.

11. An acylated cellobiose according to claim 9 wherein the R' cycloaliphatic residue comprises a cyclohexyl residue.

12. An acylated cellobiose according to claim 9 wherein X represents R—CO— in at least 6 locations and each R residue represents a linear group comprising from 7 to 11 carbons.

13. An acylated cellobiose according to claim 12 wherein the X residue is n-nonoyl.

14. An acylated cellobiose according to claim 12 wherein the R' residue is selected from the group consisting of linear alkyl residues differing from the R residue by at least 2 carbon atoms, phenyl, naphthyl or biphenyl residues and a cyclohexyl residue.

15. An acylated cellobiose according to claim 1 wherein the major fraction of the acylated cellobiose is the α anomer.

16. An acylated cellobiose according to claim 1 wherein the major fraction of the acylated cellobiose is the β anomer.

17. An acylated cellobiose according to claim 1 wherein not more than 50% of the Z residue represents H.

18. An acylated cellobiose according to claim 17 wherein not more than 25% of the Z residue represents H.

19. An acylated cellobiose according to claim 1 which is selected from cellobiose heptanonanoate monobenzoate, cellobiose heptanonanoate mononaphthanoate, cellobiose heptanonanoate monoethanoate, and cellobiose heptanonanoate monocyclohexanoate.

20. An acylated cellobiose according to claim 1 which is selected from cellobiose heptadecanoate monobenzoate, cellobiose heptadecanoate monobiphenyloate, cellobiose heptadecanoate monoethanoate, and cellobiose heptadecanoate monocyclohexanoate.

21. An acylated cellobiose according to claim 1 wherein at least 90% of the acylated cellobiose is the β anomer.

22. An acylated cellobiose according to claim 1 wherein at least 90% of the acylated cellobiose is the β anomer.

23. A cream, soft solid or solid composition comprising a water-immiscible liquid structured or thickened by an effective amount of a gellant in which the gellant comprises an acylated cellobiose (CHME) as specified in claim 1.

24. A composition according to claim 23 which contains the gellant in an amount selected in the range of from 0.1 to 20% by weight of its combined weight with the water-immiscible liquid.

25. A composition according to claim 23 in which said acylated cellobiose CHME represents a major fraction of the gellant.

26. A composition according to claim 23 in which said CHME ester is a cellobiose heptanonanoate monocyclohexanoate ester.

27. A composition according to claim 23 in which said acylated cellobiose CHME is employed in conjunction with a gellant (ACB) that is represented by the formula:

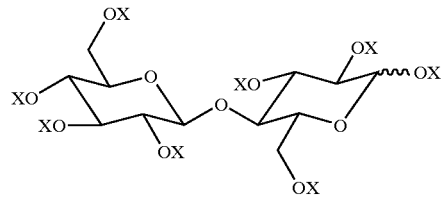

in which X represents an acyl group (R—CO—) or H, H being not more than a minority of X residues and R represents a saturated or unsaturated, linear or branched chain hydrocarbon residue containing from 5 to 31 carbon atoms.

28. A composition according to claim 27 in which said acylated cellobiose CHME is employed in a weight ratio to said ACB of from 25:1 to 1:25.

29. A composition according to claim 27 in which said CHME and said ACB are present in a weight ratio in the range of from 15:85 to 35:65.

30. A composition according to claim 29 in which the CHME is at least 90 molar % β anomer and the ACB is at least 80 molar % α anomer.

31. A composition according to claim 30 in which the active agent is dissolved or suspended in the water-immiscible liquid.

32. A composition according to claim 31 in which the antiperspirant salt is selected from the group consisting of aluminium chlorohydrate, activated aluminium chlorohydrate, aluminium/zirconium chlorohydrate and a complex of aluminium and zirconium chlorohydrate with glycine.

33. A composition according to claim 31 in which the antiperspirant is suspended in the water-immiscible liquid and the composition is translucent.

34. A composition according to claim 30 in which said personal care agent comprises an antiperspirant or a deodorant.

35. A composition according to claim 27 in which the CHME comprises cellobiose heptadecanoate mono benzoate and the ACB comprises cellobiose octadecanoate.

36. A composition according to claim 27 in which said acylated cellobiose CHME is employed in a weight ratio to said ACB of from 1:1 to 1:12.

37. A composition according to claim 23 which additionally contains one or more active agents selected from skin benefit agents, personal care agents, medicaments, sunscreen or tanning aid.

38. A composition according to claim 37 in which the one or more active agent is dissolved in the aqueous or water-miscible liquid.

39. A composition according to claim 37 in which the one or more active agent comprises an antiperspirant salt.

40. A composition according to claim 39 in which the antiperspirant salt comprises an aluminium salt or an aluminium and zirconium salt.

41. A composition according to claim 39 in which the antiperspirant salt is selected from aluminium chlorohydrate, aluminium/zirconium chlorohydrate and a complex of aluminium and zirconium chlorohydrate with glycine.

42. A composition according to claim 23 in which the thickened or structured water-immiscible liquid forms an emulsion or micro-emulsion with an aqueous or water-miscible liquid.

43. A composition according to claim 42 in which the emulsion is a water-in-oil emulsion.

44. A composition according to claim 43 in which the emulsion is a transparent or translucent stick.

45. A composition according to claim 42 in which the emulsion is transparent or translucent.

46. A composition according to claim 23 which contains the gellant in an amount selected in the range of from 0.5 to 15% by weight of its combined weight with the water-immiscible liquid.

47. Cosmetic use of a composition according to claim 23 in which the composition is applied topically to skin.

48. A method for preparing an acylated cellobiose according to claim 1 comprising the step of reacting an acylated cellobiose having formula 2:

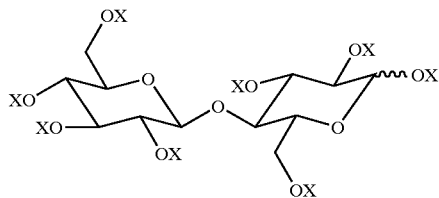

in which X represents an acyl group (R—CO—) or H, at the anomeric carbon of the cellobiose and in one other location and an R—CO-group in 6 other locations, and R represents a saturated or unsaturated, linear or branched chain hydrocarbon residue containing from 7 to 11 carbon atoms with an acylating agent containing a residue R' as described in claim 1 preferentially at the anomeric carbon of the cellobiose.

49. A method according to claim 48 characterised by first reacting cellobiose with an acylating agent containing a residue R as described in claim 1 in an amount such that a majority of hydroxyl substituents in the cellobiose are acylated, including the hydroxyl group at its anomeric carbon atom, secondly, at least partially deacylating the product of the first step at the anomeric carbon in the cellobiose and thereafter in a third step reacting the product of the second step with an acylating agent containing the residue R'.

50. A method according to claim 48 wherein the acylating agent employed for acylating at the anomeric carbon is an acid chloride or carboxylic acid anhydride or carboxylic acid/strong acid anhydride catalyst.

51. A method of thickening or structuring a water-immiscible liquid to form a cream, soft solid or solid comprising the steps of forming a solution of a gellant in the water-immiscible liquid at a temperature above the solution's gelling temperature and thereafter cooling the solution to and maintaining the solution at below its gelling temperature until the viscosity of the solution has increased or until the solution has solidified wherein the gellant comprises an acylated cellobiose (CHME) as specified in claim 1.

* * * * *